US007075653B1

(12) United States Patent
Rutherford

(10) Patent No.: US 7,075,653 B1
(45) Date of Patent: Jul. 11, 2006

(54) METHOD AND APPARATUS FOR LASER-BASED REMOTE METHANE LEAK DETECTION

(75) Inventor: James M. Rutherford, Cypress, TX (US)

(73) Assignee: Heath Consultants Incorporated, Houston, TX (US)

( * ) Notice: Subject to any disclaimer, the term of this patent is extended or adjusted under 35 U.S.C. 154(b) by 0 days.

(21) Appl. No.: 11/118,871

(22) Filed: Apr. 29, 2005

(51) Int. Cl.
*G01N 21/61* (2006.01)
*G01F 1/66* (2006.01)

(52) U.S. Cl. ............... 356/437; 356/432; 250/339.11; 250/338.5; 73/40.5 A; 73/861.27

(58) Field of Classification Search ........ 356/432–444; 250/338.1, 338.5, 339.1, 339.11, 458.1, 459.1; 73/40.5, 592, 861.27, 335.01
See application file for complete search history.

(56) References Cited

U.S. PATENT DOCUMENTS

| | | | | |
|---|---|---|---|---|
| 3,662,171 A | * | 5/1972 | Brengman et al. | 250/342 |
| 4,001,764 A | * | 1/1977 | Holland et al. | 367/6 |
| 4,489,239 A | * | 12/1984 | Grant et al. | 250/339.03 |
| 5,015,099 A | | 5/1991 | Nagai et al. | |
| 5,202,570 A | | 4/1993 | Tanaka et al. | |
| 5,430,293 A | * | 7/1995 | Sato et al. | 250/330 |
| 6,725,705 B1 | * | 4/2004 | Huebler et al. | 73/40.5 A |
| 6,750,453 B1 | * | 6/2004 | Nelson et al. | 250/338.5 |
| 6,822,742 B1 | * | 11/2004 | Kalayeh et al. | 356/437 |

FOREIGN PATENT DOCUMENTS

EP 0489546 A2 * 11/1991

OTHER PUBLICATIONS

PSI Newsletter; "PSI's Technologies Assist with Homeland Security"; 2004, Issue 1; a publication of Physical Sciences Inc. USA.
Takaya Iseki; "Lasermethane™—a Portable Remote Methane Detector"; R&D Division, Technology Development Dept., Sensing & Controls Center, Tokyo Gas Co., Ltd.
Mickey B. Frish; "High-Altitude Aerial Natural Gas Leak Detection System, Technology Status Assessment"; Physical Sciences Inc., 20 New England Business Center, Andover, MA USA 01810-1077; Dec. 2004.
M.B. Frish, R.T. Wainner, B.D. Green, J. Stafford-Evans, M.C. Laderer, M.G. Allen; "Progress in Reducing Size and Cost of Trace Gas Analyzers Based on Tunable Diode Laser Absorption Spectroscopy"; Physical Sciences Inc., 20 New England Business Center, Andover, MA USA 01810-1077.

* cited by examiner

*Primary Examiner*—Gregory J. Toatley, Jr.
*Assistant Examiner*—Sang H. Nguyen
(74) *Attorney, Agent, or Firm*—Gary L. Bush, Esq.; Andrews Kurth LLP

(57) ABSTRACT

A method and apparatus for remote laser-based detection of gas at levels exceeding natural background levels preferably utilizing wavelength modulated tunable diode laser absorption spectroscopy. In a preferred embodiment, background gas and noise are estimated using statistical moving average and variance calculations. Gas concentration length measurements resulting from the spectroscopy are preferably compared in real-time or near-real-time to the sum of the background and noise estimates and an alarm limit to detect gas presence of concern. Gas levels exceeding this detection threshold are preferably indicated by a prolonged output tone with a pitch indicative of the magnitude of the gas measurement, and gas levels below the detection threshold are preferably indicated by silence.

18 Claims, 11 Drawing Sheets

METHOD AND APPARATUS FOR LASER-BASED REMOTE METHANE LEAK DETECTION

BACKGROUND OF THE INVENTION

1. Field of the Invention

This invention relates generally to leak detection and specifically to detection of methane gas, particularly for use in conducting routine surveys of natural gas utility pipelines.

2. Description of the Prior Art

Natural gas utility companies operate approximately 61 million customer gas meters in the United States alone, supplied by over one million miles of pipeline, 17 hundred transmission stations and 17 thousand compressors. To maintain security and integrity of this vast distribution system and to comply with regulatory requirements, gas pipelines are subject to regular inspections to detect leaks. Routine periodic leak surveys are typically accomplished by a walking survey, a mobile survey or an aerial survey, and it is estimated that the natural gas distribution and transmission industry spends over $300 million annually to survey the pipeline network for leaks. Because varying trace levels of methane, ethane, propane and butane are found in the atmosphere from decaying organic material, flatulence, et cetera, survey instruments must be capable of distinguishing naturally occurring background gas levels from levels indicative of a natural gas pipeline leak.

Surveys are generally performed using one or more detectors relying on varying detection methods and principles. For example, combustible gas indicators (CGIs), which sense all combustible gases, may be used for walking surveys. CGIs work on the principle of catalytic combustion of a gas sample. They are generally unable to detect gas mixtures much below the lower combustible concentration limit, and thus they have generally low sensitivity and do not readily detect low gas concentrations. Additionally, the sample probe must be located within the gas plume in order for the CGI to obtain a reading. Therefore, CGIs are generally suitable only for walking surveys where the operator can move the probe along the entire length of the gas line.

A more sensitive leak detector commonly used is the flame ionization detector (FID). The FID operates on the principle of measuring electrical conductivity of a flame burning carbon compounds. Like the CGIs, FIDs sense all combustible gases and require the sampling probe to be placed within the gas plume in order to detect the gas leak. However, while the CGI typically measures gas concentration in percentage, the FID typically measures gas concentration in parts per million (ppm). The FID is useful for walking, mobile and airborne surveys, but only by traveling through the leak plume.

The CGI and FID both typically use an extractive sample or measurement path. In this method, target gas concentration is measured by a detector installed in a measurement chamber through which gases of interest are continually drawn from the immediate surrounding atmosphere via the probe. There is generally a detection delay of a few seconds associated with the time required to draw the gas sample into the measurement chamber.

An optical methane detector (OMD) operates by absorption of infrared light by methane. Because natural gas primarily contains methane gas, detection of methane gas serves for detection of natural gas. It is well known that gas molecules absorb energy in narrow bands surrounding specific wavelengths in the electromagnetic frequency spectrum. For example, methane has strong absorption bands at 1.33 μm, 1.67 μm, 3.3 μm, and 7.6 μm. At wavelengths falling even slightly outside the narrow absorption band, there is essentially no absorption. Thus, the OMD measures the attenuation of an infrared light source passing through a gas sample at the methane-characteristic absorption wavelength to determine the presence of methane gas. Therefore, the OMD is more selective than either the CGI or the FID, because it measures methane specifically and not all combustible gases. The OMD generally uses a short open path sample method which eliminates the sampling time delay associated with extractive sampling method of CGIs or FIDs. In a short open path configuration, the light source is transmitted across a line of sight and is either reflected to an optical detector by a fixed reflector of known characteristics located only a short distance from the light source, or the light is received directly by a fixed detector located only a short distance away from the light source. The OMD sensitivity in detecting methane is of the same order of magnitude as the FID. However, the short open probe must still be immersed in the leak plume for detection to occur. Therefore, like the FID, the OMD is useful for walking, mobile or airborne surveys only by traveling through the leak plume.

During a walking survey, a person walks above the service line and uses an instrument to detect gas escaping from the pipe, meters, fittings, etc. Because the commonly available gas detectors such as CGIs, FIDs or OMDs must be positioned within the leak plume to detect the presence of methane, a service person must usually walk the entire length of the service line between the main and the customer gas meter to ensure that low level gas emissions are not missed. The procedure may be arduous, particularly when access to private property is involved. The walking surveys not only require the surveyor to know fairly accurately where the gas pipe is under the ground, but may also require access to residential or business property to properly survey the entire system. Obstacles such as fences and dogs can be problematic.

In a mobile survey, a vehicle is driven as close to the pipe as possible while the vehicle remains on the right-of-way. FIDs or OMDs are used to detect gas escaping from the pipe, meters, fittings, etc. and collecting in plumes which cross the right-of-way. Unless the leak is located close to the right-of-way or a fortuitous breeze exists, the plume must generally be large in order to reach the right of way and hence is likely to be of lower concentration and more difficult to detect.

For an aerial survey, an aircraft flies at a low altitude along the right-of-way using visual, flame ionization or infrared techniques to identify major sources of gas leakage along the route of the gas pipe. Aerial surveys in general are used to identify larger emissions. These larger emissions may cause major vegetation discoloration or disruptions to the pipe cover. Aerial surveys with gas detection instruments rely on the fact that natural gas is lighter than air and will rise into the atmosphere where it may possibly be detected by an instrument mounted on the aircraft.

Both the flame ionization and infrared detector instruments require that readings be made near the source of the emission or that a representative sample of the atmosphere above the gas pipe be received within a sensor for indication. However, a recently developed technology, referred to herein as a laser methane detector, which uses wavelength-modulated laser absorption spectroscopy, specifically tunable diode laser absorption spectroscopy (TDLAS), may greatly simplify and economize walking and mobile surveys. Referring to FIG. 1, laser methane detectors (10)

containing a tunable diode laser, an optical detector capable of detecting the reflected light emitted from the laser, and associated detection circuitry, can be used by a technician (12) to survey a gas line installation (14) from a distance. Laser methane detectors significantly reduce the need for the surveyor to gain access to private property (16) and walk the entire length of the service pipe (14) to complete the survey, thus realizing an estimated productivity improvement of between twenty and forty percent.

TDLAS gas analyzers rely on well-known spectroscopic principles and sensitive detection techniques coupled with advanced diode lasers. Gas molecules absorb energy in narrow bands surrounding specific wavelengths (sometimes referred to as absorption lines) in the electromagnetic spectrum. At wavelengths slightly different than the narrow absorption bands, there is essentially no absorption. Specifically, when the laser wavelength is tuned to correspond to a particular absorption band of a target gas molecule, the light transmitted across a measurement path containing the gas is attenuated according to the Lambert-Beer relation, $$I_v = I_{v,o} e^{-S(T)g(v-v_o)Nl} \quad (1)$$

where:
- $I_v$ is the received intensity;
- $I_{v,o}$ is the initial laser intensity;
- $v$ is the laser frequency;
- $l$ is the optical path length through the gas;
- $S(T)$ is the temperature-dependent absorption line strength;
- $N$ is the target species number density; and
- $g(v - v_o)$ is the lineshape function which describes the frequency dependence of the absorption line strength.

The argument of the exponential function is the fractional change in the laser intensity across the measurement path and is conventionally known as the absorbance. By transmitting a beam of light (18) through a gas mixture sample containing a quantity of the target gas (20), tuning the beam's wavelength to one of the target gas's absorption bands, and accurately measuring the absorption of that beam, the concentration of target gas molecules integrated over the beam's path length, l, can be accurately determined.

Until the 1990s, TDLAS was suitable only for laboratory-based gas analysis, because it required highly-skilled individuals to operate and maintain the complex devices and provide expert interpretation of the results. During the past decade, however, the technology has developed primarily because of the advent of reliable monochromatic near-infrared (1.2–2.5 µm) diode lasers that operate continuously and unattended at room temperature without cooling by liquid nitrogen. These lasers, particularly the distributed feedback variety with grating-like optical elements which force each laser to emit light at a specified wavelength, offer line widths less than 0.003 cm$^{-1}$, which is considerably narrower than molecular absorption line widths (typically 0.1 cm$^{-1}$ at atmospheric conditions). By accurately controlling the laser temperature and current, the laser wavelength may be rapidly and precisely tuned over a range of about ±2 nm around its specified wavelength. Similarly, vertical cavity surface emitting lasers provide suitable performance characteristics in the 700–900 nm wavelength range.

With laser methane detectors (Applicant's assignee, Heath Consultants, uses a trademark, RMLD, to designate its version of a laser methane detector), a tunable diode laser beam (18) is transmitted onto a distant (e.g., up to 100 feet) topographic target (22). Some of the laser light (24) is reflected by the target back to an optical detector co-located with the laser in the laser methane detector in what is referred to as a stand-off measurement path. The laser has a specific design wavelength chosen to optimize the sensitivity to methane gas (e.g., 1.6537 µm, a wavelength corresponding to an absorption line of methane which is also free of interfering absorption from other molecules). The laser's fast tuning capability is exploited to rapidly and repeatedly scan the wavelength across the gas absorption line. While this scanning occurs, the fraction of emitted laser power that is transmitted through the gas mixture and reflected back to the instrument is received and measured by the optical detector. When the wavelength is tuned outside of the narrow characteristic absorption band ("off-line"), the received light is equal to or greater than when it falls within the narrow absorption band ("on-line"). Measurement of the relative amplitudes of off-line to on-line reception yields a precise and highly sensitive measure of the concentration of the methane gas along the path transited by the laser beam. The collected light is converted to an electrical signal, which is processed so that methane column density (the methane concentration integrated over the beam length) can be reported, usually in ppm·m. Typically, the laser methane detector rapidly processes discreet measurements at a refresh rate, e.g., of 10 Hz.

Referring to FIG. 2, an laser methane detector (10) generally includes a number of functionally interactive components: a laser emitter subsystem (30) that contains a laser source module and electronic modules that synthesize the laser modulation and control signals; an optical detector (32), e.g., a photodiode; a signal processing module (34) which contains the electronic components that extract the absorption signal information from the optical detector's output; a system controller (36) (usually microprocessor-based); and a user interface module (38), e.g., a LCD alphanumeric display or audio output. The laser beam transmitter and receiver may be placed in a combined optical assembly (not shown). laser methane detectors (10) are typically packaged into a hand-held gun (40) including an optical transceiver and an alphanumeric display and a shoulder or waist-mounted unit (42) with some controller circuitry (36) and a rechargeable battery pack (37). The two sections (40, 42) are generally connected by an umbilical cable (44) with optical fibers and electrical wires.

Some laser methane detectors currently employ an audio tone user interface in order to aid the user in identifying gas leaks from natural background methane levels. As the detected methane level increases, the output tone linearly increases in pitch, for example, according to the equation $$T = \begin{cases} c \cdot M = c \cdot k(f_2/f_1) & \text{for } f_1 \geq 10 \text{ or } f_2 \geq 0.5 \\ 0 & \text{for } f_1 < 10 \text{ and } f_2 < 0.5 \end{cases} \quad (2)$$

where:
- $T$ is the output tone level (Hz);
- $M$ is the calculated methane column density (ppm · m);
- $c$ is a tone coefficient, typically 10 Hz/ppm · m;
- $f_1$ is the off-line reflection intensity;
- $f_2$ is the on-line reflection intensity; and
- $k$ is a conversion constant.

If both the off-line and on-line return intensities are too low, the laser methane detector outputs no tone to indicate a low-light condition. Otherwise, the user may become crazed by a continuous cannonade of cacophonous tones. The frequency of the tone changes from sample to sample, causing the user to perceive noise. The user of the instrument must then be able to distinguish tone pitch changes that are indicative of a gas leak. Because the tone level increases with the detected methane, high gas concentrations are generally easy for an operator to recognize, but more subtle pitch changes indicative of smaller leaks may go unnoticed. Because the user is forced to carefully listen to discordant tones throughout the entire survey, surveying can be particularly fatiguing for the user.

Additionally, there are several characteristics of stand-off detection that hamper the user's ability to distinguish background methane from methane resulting from a natural gas leak. First, even with constant natural background methane levels, as the scanning distance increases, the methane column density (methane concentration—beam length product) measured by the laser methane detector increases, causing the output tone pitch to rise. In other words, as the scan distance increases, the laser beam passes through more natural methane background, and the tone pitch increases. Second, the variance in the reflected light levels at the laser methane detector increases as the scanning distance increases causing the tone pitch to more rapidly change up and down. This phenomenon may be due in part to increased deflection and backscatter of both off-line and on-line signals as the light passes through more atmosphere. Third, changes in the reflectance of the various topographical surfaces increases the variance in the received light levels at the laser methane detector. For example, when the scan crosses a sharp transition between two different surface types, such as an asphalt-grass interface, a high pitch tone may be heard even though there is no gas leak.

Further, other difficulties hamper detection of gas leaks. First, beam power, size, and calibration of the instrument all affect the detection effectiveness. Second, with too low a signal/tonal update rate, the user may miss a very short "hit" of one or two samples. Third, the digital display is of limited assistance in finding small leaks due to a slow screen update rate (typically 3 Hz), and the fact that it is difficult to focus simultaneously both on where the laser beam is being directed and the digital display.

Because of these limitations and characteristics, most users find it difficult to discern a leak by tonal difference when there is a high background signal or for low level leaks. The ability of a user to discern a subtle tonal change when the background is high and when there is a high variance, e.g. during long scanning distances, is very difficult if not impossible. The ability to discriminate leaks based on tone change is also dependent on the user's hearing ability, and experience in listening to the tonal response under different conditions. In addition, differences in sound from unit to unit may make it more difficult for a user to switch between units with equal results.

A laser methane detector having sophisticated data processing capabilities which take into account signature and signal characteristics to enhance a user's ability to detect a gas leak over reliance simply on tones generated from raw methane column density data is desirable.

3. Identification of Objects and Features of the Invention

An object of the invention is to provide a method for optical leak detection and an optical detector therefor that uses statistical data analysis in real-time or near-real-time to aid the user while surveying in the field to differentiate gas levels greater than the general background levels, and possibly indicative of a leak or of interest, from background gas levels.

Another object of the invention is to provide a method for optical leak detection and an optical detector therefor which does not need to be located within the gas leak plume in order to detect a leak and which is suitable for walking surveys.

Another object of the invention is to provide a method for optical leak detection and an optical detector therefor which promotes user comfort, enhances leak identification and reduces user fatigue by outputting audio tones for detected gas levels of interest and silence at lower gas levels.

Another object of the invention is to provide a method for optical leak detection and an optical detector therefor which can detect methane plumes with a concentration as low as 5 ppm-m and as far away as 100 ft.

Another object of the invention is to provide a method for optical leak detection and an optical detector therefor which is sensitive under varying weather conditions.

Another object of the invention is to provide a method for optical leak detection and an optical detector therefor which may be handheld.

SUMMARY

The objects identified above, as well as other advantages and features of the invention are incorporated in a preferred embodiment of the invention in methods and apparatus for detecting the presence of gas, usually methane. A light beam from a laser having a wavelength generally corresponding to an absorption band of the gas illuminates a target. A received portion of the light beam is reflected from the target to a detector. The received portion of the light beam is sampled to produce a series of measurements which represent a concentration length product of the gas through which the received portion of the light beam has traveled. A detection threshold is periodically determined from a statistical analysis of the series of measurements which estimates a threshold level above which a current measurement of the series of measurements is significant. The current measurement of the series of measurements is compared with a most recent determination of the detection threshold. A signal is produced which indicates the pressure of gas at a level greater than the threshold level when the current measurement exceeds the most recent determination of the detection threshold.

BRIEF DESCRIPTION OF THE DRAWINGS

One or more embodiments of the invention are described in detail hereinafter as illustrated in the accompanying figures, in which.

DESCRIPTION OF THE PREFERRED EMBODIMENT OF THE INVENTION

Figure 1:
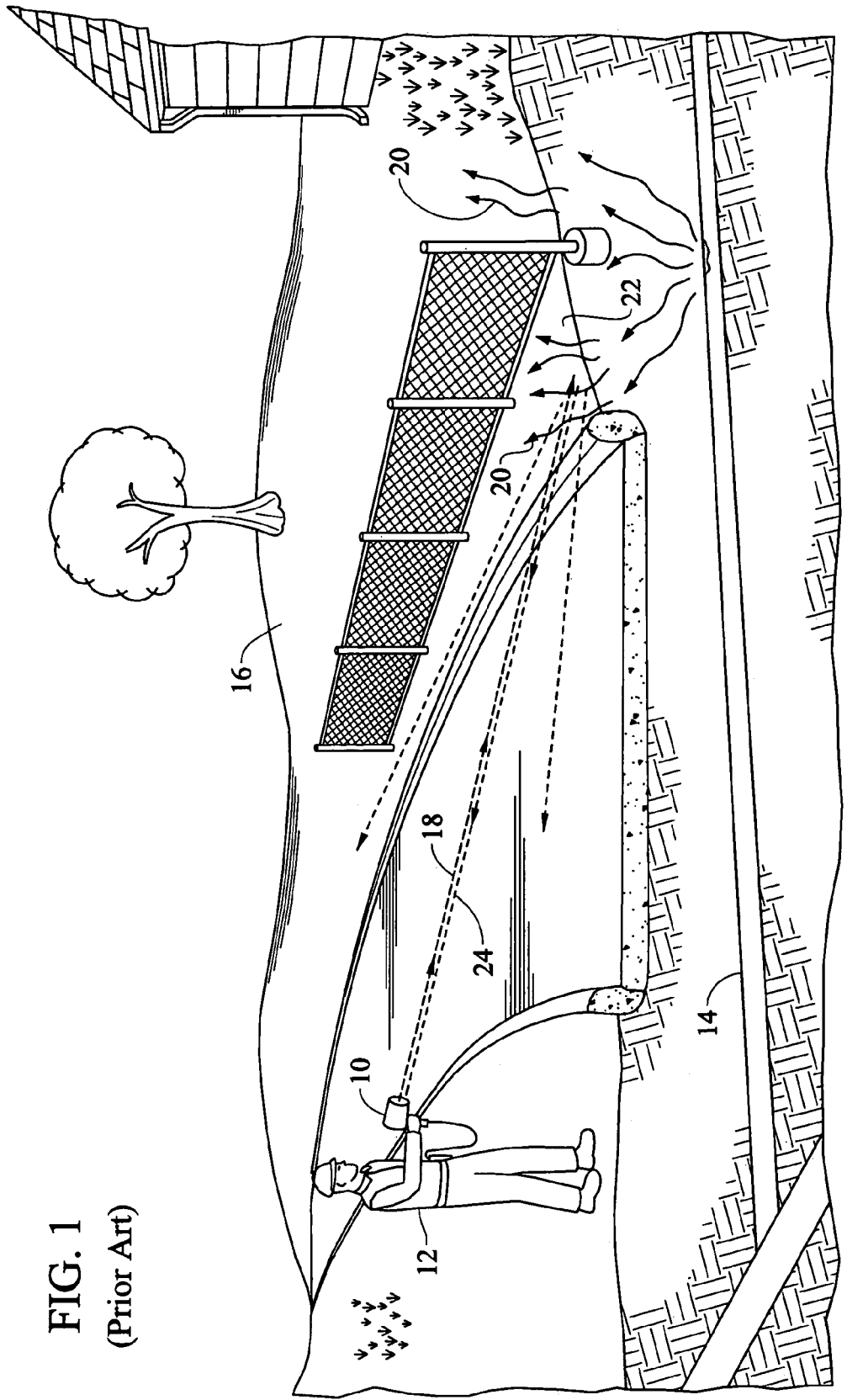
FIG. 1 illustrates a typical prior art method of using a laser methane detector in a stand-off survey where a user shines a laser beam at a distant topographic target and a reflection is measured to determine the methane column density through which the laser beam passes.
Figure 2:
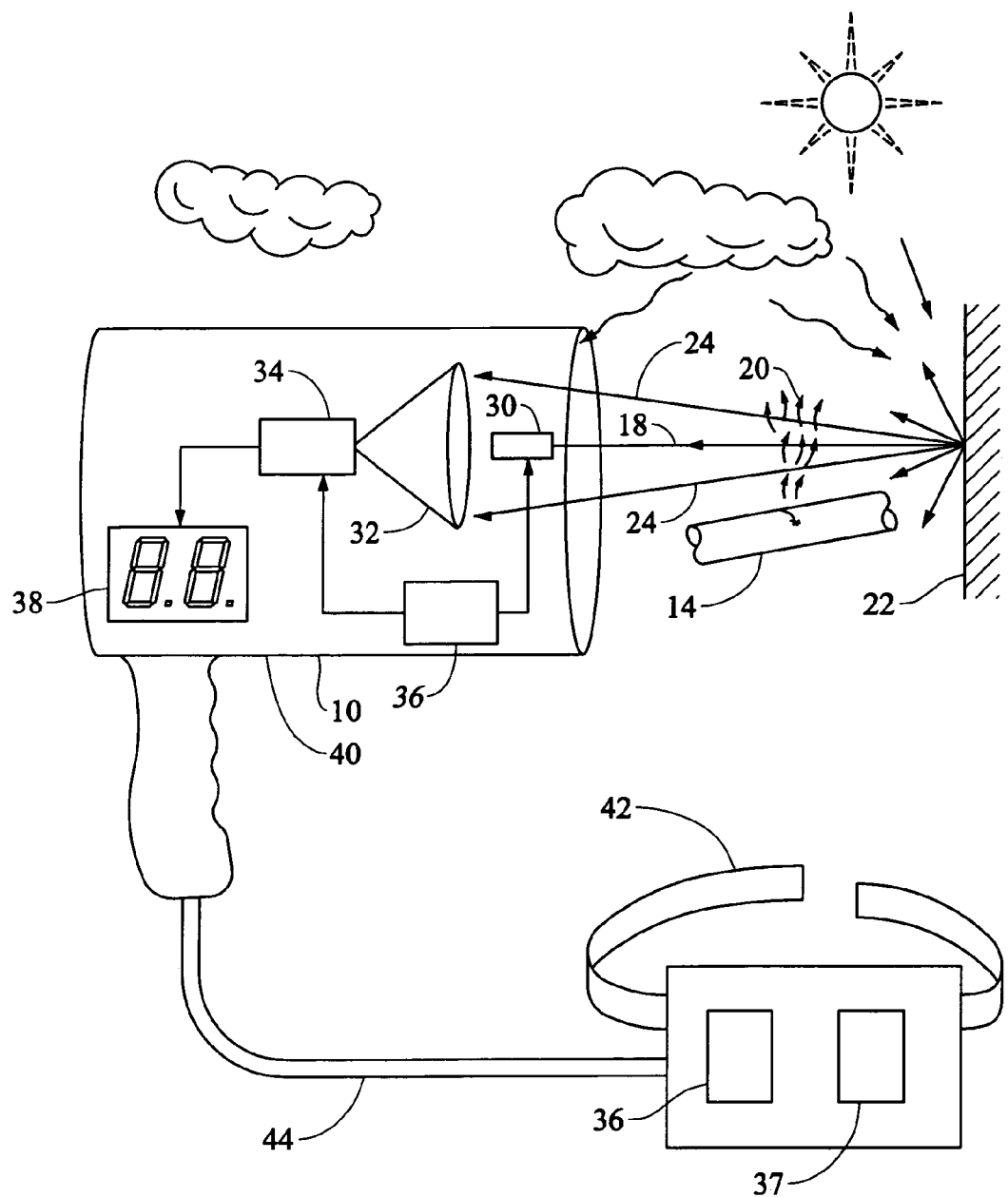
FIG. 2 is a schematic illustrating a typical prior art laser methane detector showing a hand-held gun having a laser, an optical detector, and a visual output display and showing a shoulder or waist-mounted controller and battery pack.
Figure 3:
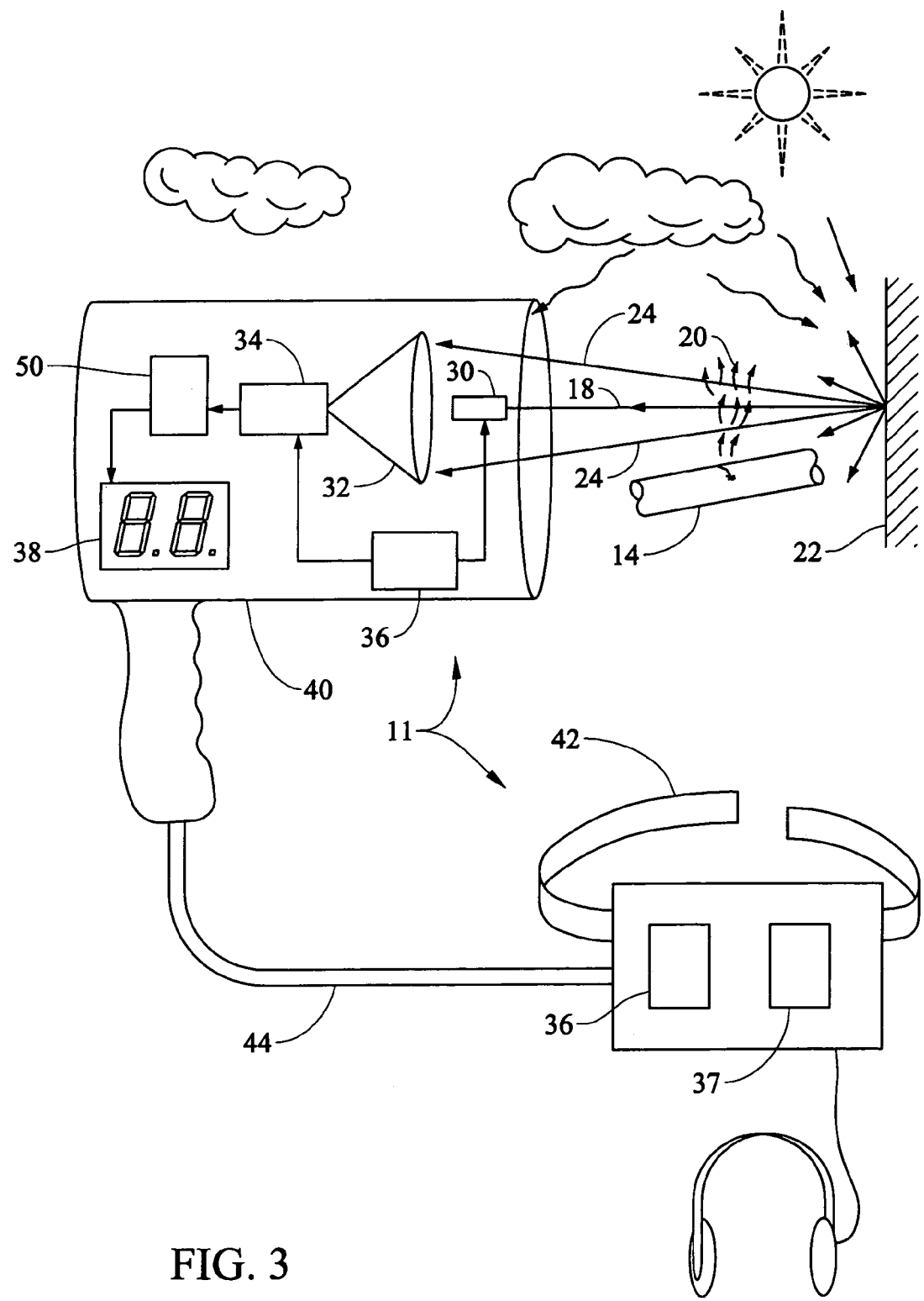
FIG. 3 is a schematic illustrating a laser methane detector according to one embodiment of the invention showing a laser methane detector similar to that of FIG. 2 but including a statistical methane detector element therein.

Referring to FIG. 3, a laser methane detector 11 of the preferred embodiment ideally includes a number of functionally interactive components: a laser emitter subsystem 30 that contains a tunable diode laser source module and electronic modules that synthesize the laser modulation and control signals; an optical detector 32, e.g., a photodiode; a signal processing module 34 which contains the electronic components that extract the absorption signal information from the optical detector's output; a system controller 36; a rechargeable battery pack 37; and a statistical methane detection processor module 50. The laser methane detector is preferably packaged into a two-piece system including a hand-held gun 40 (having the laser 30 and detector 32 (combined into an optical transceiver) and a LCD alphanumeric display 38) and a shoulder or waist-mounted controller/battery pack unit 42. The two sections 40, 42 are preferably connected by an umbilical cable 44 having optical fibers and electrical wires. The statistical methane detection processor module 50 is preferably implemented using a microprocessor or microcontroller with sufficient memory, speed and processing capacity to perform the desired statistical calculations, for example, the background and noise estimate algorithms described herein, in real-time or near-real-time. The statistical detection processor 50 preferably has an input section for receiving methane column density data, a processing section with software, memory and processor for performing calculations, and an output section. It is preferably controlled by the system controller 36. The methane detection processor 50 may be separate from or may be integrated with the signal processor 34. Because the art of microprocessors, microcontroller, and the programming thereof is extensively known, the details of such are not discussed further herein.

In the preferred embodiment, a tunable diode laser 30 transmits a beam 18 is transmitted onto a distant (e.g., 100 feet) topographic target 22. Some of the laser light 24 is reflected by the target back to an optical detector 32 co-located with the laser 30 in the laser methane detector 11 in what is referred to as a stand-off measurement path. The laser 30 has a specific design wavelength chosen to optimize the sensitivity to methane gas (or the gas of interest). The laser's fast tuning capability is exploited to rapidly and repeatedly scan the wavelength across the gas absorption line. While this scanning occurs, the fraction 24 of emitted laser power that is transmitted through a methane leak plume 20 and through background methane in the atmosphere is reflected back to the optical detector 32. When the wavelength is tuned outside of the narrow characteristic absorption band ("off-line"), the received light 24 is equal to or greater than when it falls within the narrow absorption band ("on-line"). Accurate measurement of the relative amplitudes of off-line to on-line reception yields a precise and highly sensitive measure of the concentration of the methane gas along the path transited by the laser beam. The collected light is converted to an electrical signal, which is processed by signal processing module 34 so that methane column density (the methane concentration of background and leak plume methane integrated over the beam length) can be reported, usually in ppm·m. Preferably, the laser methane detector 11 rapidly processes discreet measurements at a refresh rate of at least 10 Hz.

To achieve high methane detection sensitivity, it is desirable to use as strong an absorption line as possible. Methane has two particularly strong absorption bands, or groups of absorption lines, centered at 3.3 μm (v3 band) and 7.6 μm (v4 band). However, based on currently available laser technology and cost constraints, a near infrared diode laser, with available wavelengths λ limited below 2.2 μm, is preferred. Below 2.2 μm, the strongest absorption band of methane is located at 1.64 to 1.70 μm (the 2v3 band). One possible absorption line is the R(3) line (λ=1.6537 μm, v=6047 cm$^{-1}$) in the 2v3 band. This line is suitable for methane leak detection since it is one of the strongest absorption lines in the 2v3 band and is free from absorption of atmospheric interference gases. Anritsu Corporation markets a Gallium Arsenide distributed feedback laser (InGaAsP DFB laser) with a wavelength suitable for spectroscopy at the R(3) absorption line.

The Lambert-Beer law expressed in Equation 1 can be re-expressed and simplified as $$I_v = K I_{v,o} e^{-D} = K I_{v,o} e^{-2\alpha M} \approx K I_{v,o} (1-2\alpha M) \quad (3)$$

where: $I_v$ is the received intensity;
$I_{v,o}$ is the initial laser intensity;
v is the laser frequency;
K is the collection efficiency (off-line $I_{v,o}/I_v$);
D is the optical depth;

-continued

| α | is the absorption coefficient (ppm$^{-1}$ · m$^{-1}$); and |
| M | is methane column density (ppm · m). |

Because the laser light is received after round-trip propagation between the laser methane detector 11 and the topographic target 22 with column density M, a factor of 2 is included in the above attenuation equation.

In a laboratory environment, powerful lasers and optimized targets can be used for spectroscopy, but for a device intended for field use by walking survey, laser power is greatly limited. Thus, the laser methane detector 11 must be arranged and designed to measure very low power levels, because it collects limited diffused reflections from a target illuminated by a low-powered laser. In a typical case, the detector 32 may receive as little as 100 nW from an initial laser power of 10 mW. In addition, the laser methane detector 11 must ideally detect minute absorptions due to methane. For example, 100 ppm·m methane corresponds to an optical depth of less than $10^{-4}$. Accurately determining the ratios between the off-line and on-line received light intensities in order to determine the methane column density is problematic at such low intensity levels. To overcome these significant technical challenges, the preferred embodiment employs second-harmonic detection techniques of wavelength modulation spectroscopy (WMS).

Figure 4:
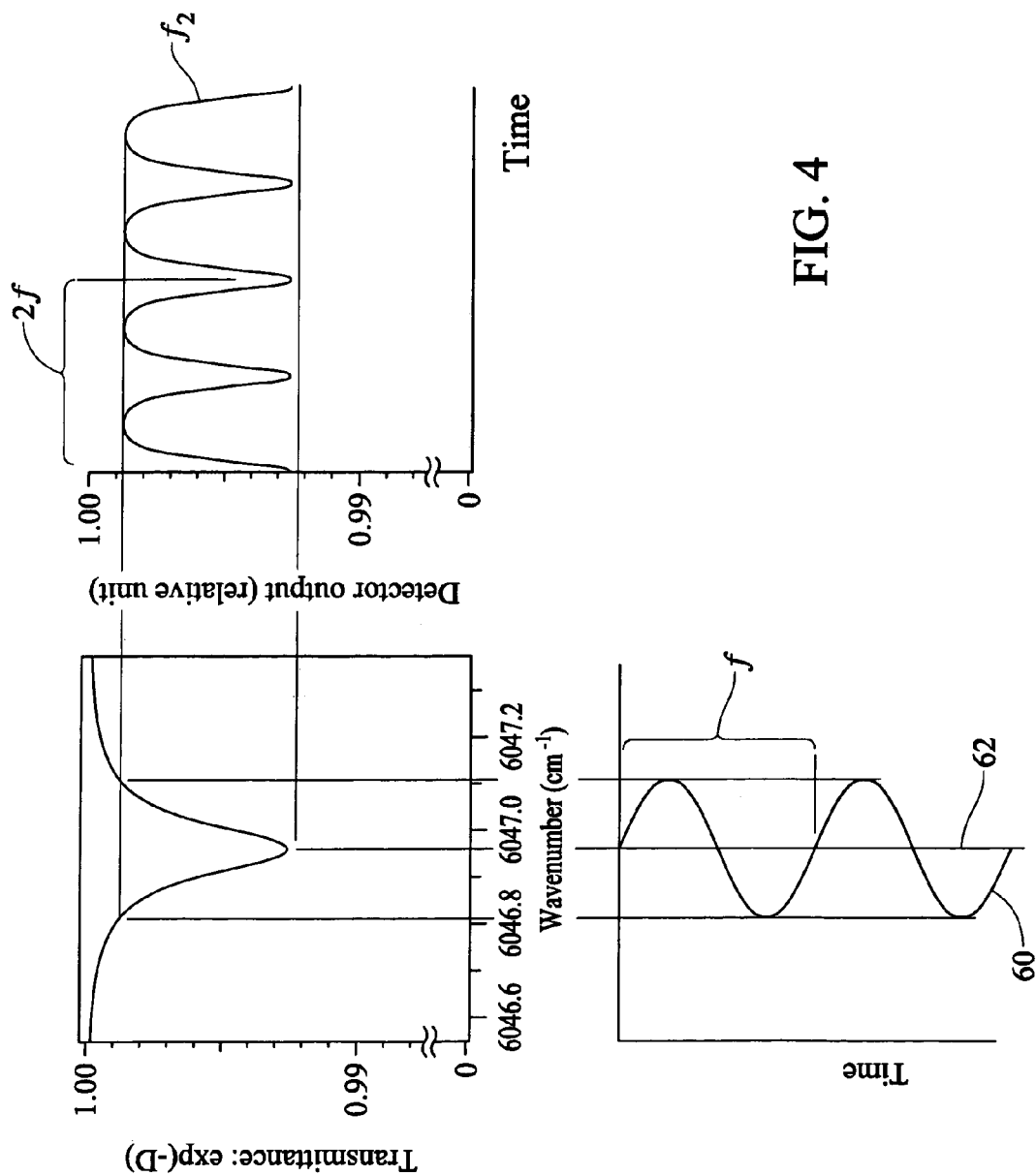
FIG. 4 is a wavelength modulation spectroscopy transfer function plot illustrating how the transmittance characteristic of a gas at its absorption band results in a second harmonic component of a frequency modulated light beam passing therethrough.

Because WMS second-harmonic detection techniques are well known in the art, only a cursory explanation is provided here. As shown in FIG. 4, the laser wavelength is modulated by a sinusoidal injection current 60 at a frequency f of preferably 10 kHz and the modulation center is located at the absorption center 62 of the 2v3 band R(3) line of methane (1.6537 μm). As a result, a second-harmonic signal $f_2$ of 20 kHz is produced in the detector output which can be sensitively measured by lock-in detection independently of the first harmonic. This $f_2$ signal is proportional to the methane column density M and is written as $$f_2 = 2 K I_{o,dc} h \alpha_o M \qquad (4)$$

| where: | $f_2$ | is the received second harmonic intensity; |
| | $I_{o,dc}$ | is the dc component of the initial laser intensity; |
| | h | is coefficient depending on modulation depth; |
| | K | is the collection efficiency (off-line $I_{v,o}/I_v$); |
| | $\alpha_o$ | is the absorption coefficient α at the absorption center; and |
| | M | is methane column density (ppm · m). |

Figure 5:
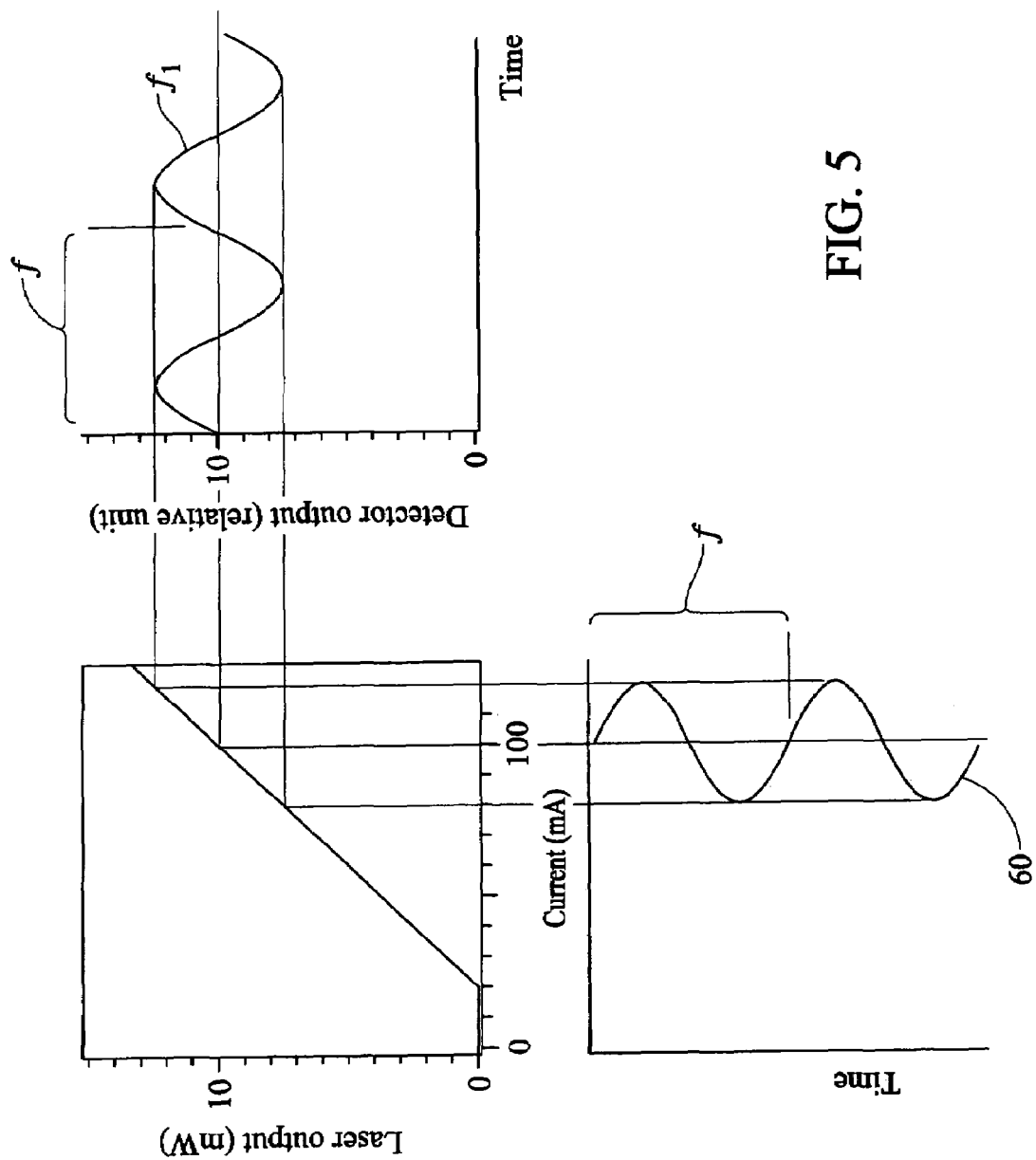
FIG. 5 is a wavelength modulation spectroscopy transfer function plot illustrating how a linear transmittance characteristic results in the fundamental frequency component of a frequency modulated light beam to be received as a reflection.

As shown in FIG. 5, the sinusoidal injection current modulates the laser power as well as the laser wavelength, and therefore the first harmonic signal $f_1$ is retained in the detector output and measured sensitively by lock-in detection independently of the second harmonic. This $f_1$ signal is independent of methane column density M and is written as $$f_1 = K I_{o,dc} m_{AM} \qquad (5)$$

| where: | $f_1$ | is the received first harmonic intensity; |
| | $I_{o,dc}$ | is the dc component of the initial laser intensity; |
| | K | is the collection efficiency (off-line $I_{v,o}/I_v$); and |
| | $m_{AM}$ | is the power modulation ratio of the laser. |

Dividing the second harmonic signal $f_2$ by the first harmonic signal $f_1$, the collection efficiency K, which changes as a function of target reflectance, distance and incident angle, is cancelled. As indicated in Equation 2 above, the methane column density M is found from the ratio between the $f_2$ and $f_1$ signals as $$M = \frac{m_{AM}}{2h\alpha_o} \frac{f_2}{f_1} = k \frac{f_2}{f_1} \qquad (6)$$

| where: | $f_1$ | is the received first harmonic intensity; |
| | $f_2$ | is the received second harmonic intensity; |
| | h | is coefficient depending on modulation depth; |
| | $\alpha_o$ | is the absorption coefficient α at the absorption center; and |
| | $m_{AM}$ | is the power modulation ratio of the laser. |

The signal processing module 34 in the preferred laser methane detector 11 calculates Equation 6, producing an output in ppm·m units. TDLAS, WMS, and laser methane detectors employing the above principles of operation are taught in U.S. Pat. No. 5,015,099 issued to Nagai et al. and U.S. Pat. No. 5,202,570 issued to Tanaka et al., both of which are incorporated herein in their entirety by reference.

In order to improve the tonal response and display limitations of current laser methane detectors, the detection algorithm performed by the statistical methane detector element 50 must compensate for negative characteristics of background noise and measurement noise inherent in stand-off scanning. For example, different surfaces have different reflectivity properties, creating different responses and resulting in higher signal variance. Also, even with constant natural background methane levels, as the scanning distance increases, the methane column density (methane concentration—beam length product) measured by the laser methane detector increases.

The preferred detection algorithm exploits several signature and signal characteristics. First, for short-range work (approximately 20 feet or less), the background methane level is generally fairly uniform and constant. Second, when the beam passes through a plume of gas emanating from a leak, a high rate of change in signal is observed. According to the invention, it is preferred to provide a statistical detection algorithm that preferably incorporates (1) a background estimator, (2) a noise estimator, (3) a user-adjustable alarm level; and (4) a minimum detection threshold computation and comparison with methane readings. However, other suitable statistical detection algorithms may be used.

Background Noise Estimation

The methane background noise estimate $B_i$ is preferably calculated by using a statistical algorithm such as a modified moving average. First, for each measurement i, a current mean methane reading $\overline{M_i}$ is calculated by averaging the n previous methane readings by $$\overline{M_i} = \frac{\sum_{x=i-n}^{i-1} M_x}{n} \qquad (7)$$

where:
- $\overline{M_i}$ is the average methane reading over the n previous readings;
- $M_i$ is the ith methane column density reading;
- i indicates the ith measurement; and
- n is the number of readings to average, preferably 10.

To estimate the background level, the current reading $M_i$ is compared to the current average methane $\overline{M_i}$. If the difference $\overline{M_i} - M_i$ exceeds a predetermined limit $\Delta M$, it may indicate a high rate of change associated with a leak, and the background estimate $B_i$ is held constant at $B_{i-1}$. Otherwise, the measurement $M_i$ is assumed to indicate to a slowly changing background. Thus, the background estimation is found by $$B_i = \begin{cases} B_i & \text{for } \overline{M_i} - M_i \leq \Delta M \\ B_{i-1} & \text{for } \overline{M_i} - M_i > \Delta M \end{cases} \quad (8)$$

where:
- $B_i$ is the estimated background methane column density for the ith reading;
- $\overline{M_i}$ is the average methane reading over the n previous readings;
- $M_i$ is the ith methane reading;
- $\Delta M$ is the background change threshold value, preferably 2 ppm · m;
- i indicates the ith measurement; and
- n is the number of readings to average, preferably 10.

It is preferred to calculate the background estimate $B_i$ for every methane measurement $M_i$, but alternatively, the background estimate may be calculated every other or every third methane measurement, for example, if desired.

The user of the preferred embodiment may have to conform the scanning tempo to the time constant of the background estimator. For example, at a rate of ten $M_i$ measurements per second, with n equal to 10, the background estimator has a one second lag. If a user suddenly moves the laser methane detector to point to a new area, rather then slowly sweeping the survey area in a smooth continuous motion, he may have to wait for the background estimator to catch up or risk erroneous survey results.

Measurement Noise Estimation

Similarly, the measurement noise is estimated by using a moving statistical technique which considers the prior m methane readings $M_i$. The current noise estimate $N_i$ is calculated using a variance calculation of the m previous methane column density readings $M_i$. A standard variance formula, $$\hat{M}_i = \sqrt{\frac{m \sum_{x=i-m}^{i-1} (M_x)^2 - \left(\sum_{x=i-m}^{i-1} M_x\right)^2}{m(m-1)}} \quad (9)$$

where:
- $\hat{M}_i$ is the standard deviation of the methane readings over the m previous readings;
- $M_i$ is the ith methane reading;
- i indicates the ith measurement; and
- m is the number of readings to consider, preferably 10, is preferred. Within a limited range, the noise estimate $N_i$ is preferably equal to the standard deviation $\hat{M}_i$. However, a lower noise limit $N_{LL}$ establishes a fundamental detection level above the background estimate, and an upper noise limit $N_{UL}$ allows for detection of rapidly changing methane readings indicative of a gas leak. Thus, the noise estimation is ideally found by $$N_i = \begin{cases} N_{LL} & \text{for } \hat{M}_i < N_{LL} \\ \hat{M}_i & \text{for } N_{LL} \leq \hat{M}_i \leq N_{UL} \\ N_{UL} & \text{for } \hat{M}_i > N_{UL} \end{cases} \quad (10)$$

where:
- $N_i$ is the estimated noise for the ith reading;
- $\hat{M}_i$ is the standard deviation of the methane readings over the previous m readings;
- $N_{LL}$ is the lower noise limit, preferably 3 ppm · m; and
- $N_{UL}$ is the upper noise limit, preferably 15 ppm · m.

Although the preferred minimum detection level $N_{LL}$ is equal to 3 ppm·m, in one embodiment, the user may be able to increase it in increments of 1. The maximum noise level $N_{UL}$ is preferably a constant equal to 15 ppm·m. It is preferred to calculate the noise estimate $N_i$ for every methane measurement $M_i$, but alternatively, the noise estimate may be calculated every other or every third methane measurement, for example, if desired. In yet another embodiment, the noise estimate $N_i$ is not limited by an upper level $N_{UL}$, a lower level $N_{LL}$, or both.

Having estimated the current background and noise levels, the method and apparatus according to a preferred embodiment ideally calculates a detection threshold $M_{DT,i}$ as $$M_{DT,i} = B_i + N_i + A_L \quad (11)$$

where:
- $M_{DT,i}$ is the detection threshold for the ith reading;
- $B_i$ is the estimated background methane column density for the ith reading;
- $N_i$ is the estimated noise for the ith reading; and
- $A_L$ is a user set variable alarm level.

When the current methane column density reading $M_i$ exceeds the current $M_{DT,i}$, a potential methane leak condition is indicated. The alarm level $A_L$ is preferably user controlled and can be set in 1 ppm·m increments from 0 to 255.

Currently the fastest laser methane detector data-logging rate is about 10 Hz. Thus, many of the preferred set points indicated herein, such as n, m, $\Delta M$, $N_{LL}$, and $N_{UL}$ for example, are based on this refresh rate. However, the method may be able to take advantage of higher data rates in order to provide better background and noise calculations, and other set point values may be suitable. Additionally, as more experience is gained using the various embodiments under various conditions, other set points values or calculations may become preferred and are included in the scope of the invention.

The set of graphs in FIGS. 6–18 illustrates how the background and noise estimate computations in the algorithm of the preferred embodiment may function under various actual leak conditions. For each graph, the measured methane column density $M_i$ is collected at a 10 Hz data logging rate without the digital methane detection circuitry according to the one or more embodiments of the invention, and then the data is plotted. Three additional curves are then calculated from the $M_i$ data and plotted on the same axes. These curves include the background estimate $B_i$, the noise estimate $N_i$, and the difference between the measured methane column density $M_i$ and the detection threshold $M_{DT,i}$ of Equation 11 where $A_L$ is set to zero. A positive $M_i-(B_i+N_i)$ value would generally represent a positive detection. The measurements where $M_i-(B_i+N_i)$ are positive are highlighted by shading for easier viewing. The graphs of FIGS. 6–18 result from use of the detection algorithm where for the background estimate, n=6, and for the noise estimate, m=3. However, other values may be suitable. The initial values for the background estimate, the noise estimate, and $M_i-(B_i+N_i)$ are set to zero until a sufficient number of data points are available for calculation (0.6 seconds).

Figure 6:
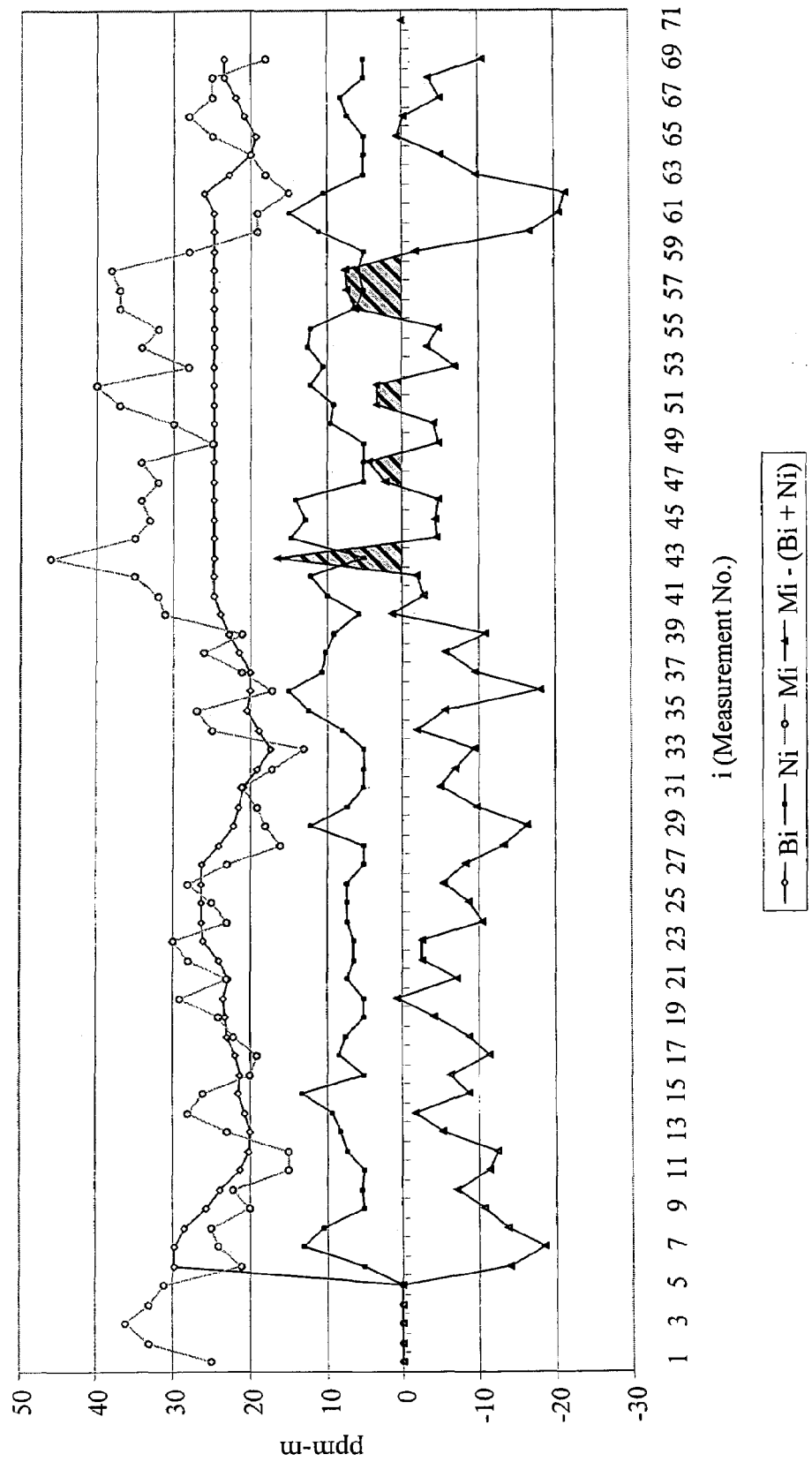
FIG. 6 is a line graph of some of the digital methane detection algorithm parameters according to one embodiment of the invention in response to laser methane detector scanning of a 100 ppm leak in a roadside curb joint where the scan occurred across from the face of the curb at a 90 degree angle from the opposite side of the street.
Figure 7:
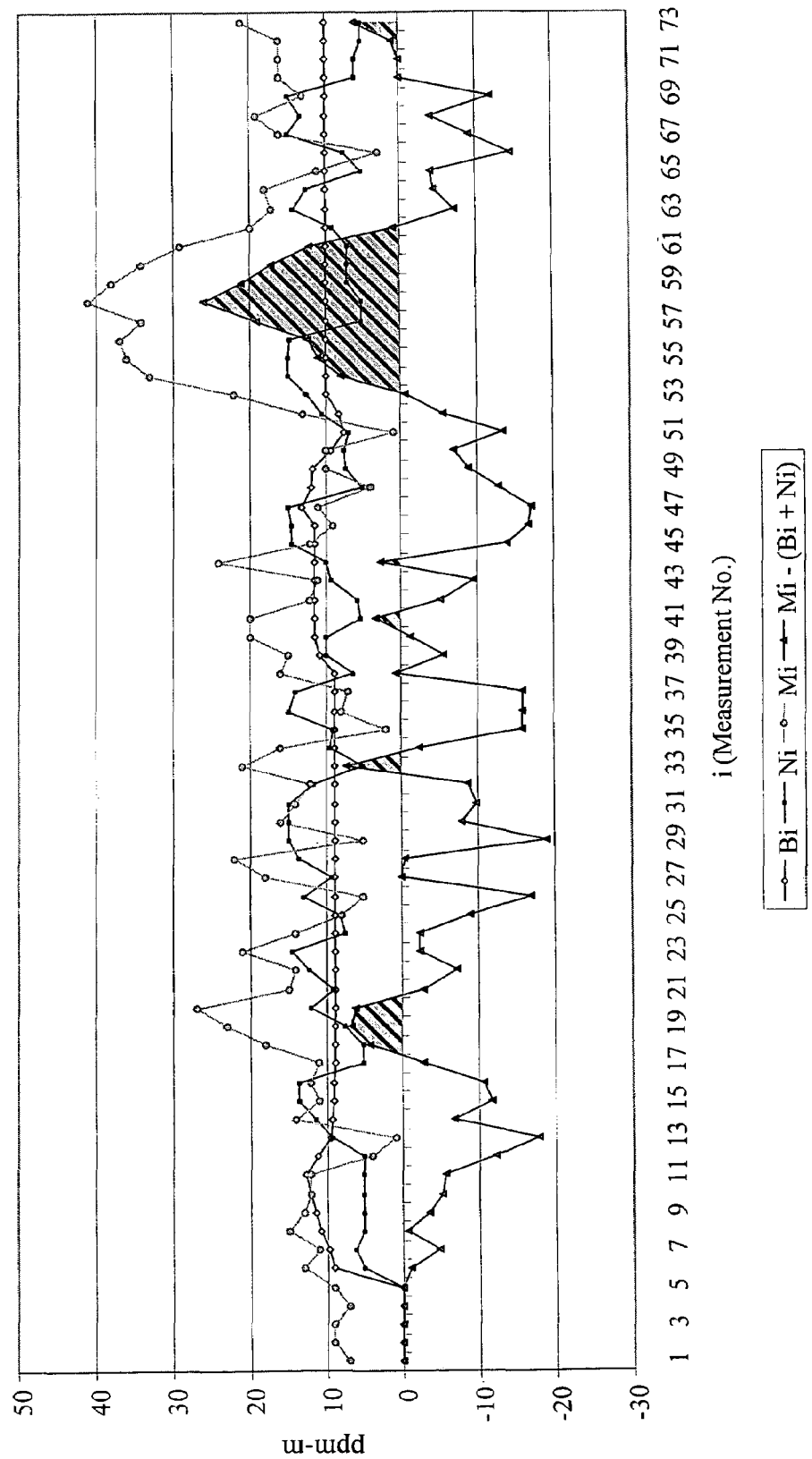
FIG. 7 is a line graph of some of the digital methane detection algorithm parameters according to one embodiment of the invention in response to laser methane detector scanning of the leak of FIG. 6 where the scan occurred at a 45 degree angle about 25 feet from the leak.
Figure 8:
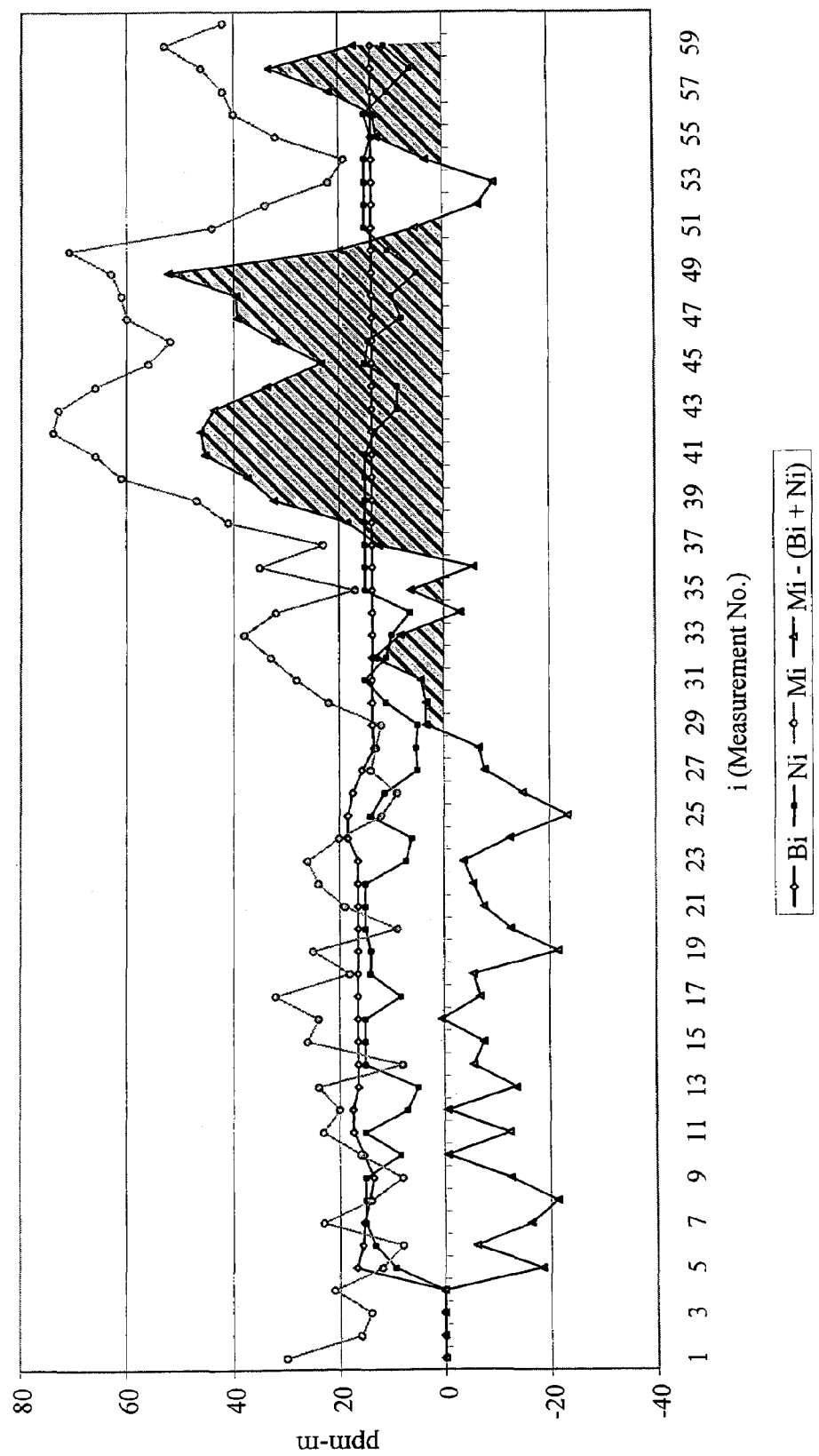
FIG. 8 is a line graph of some of the digital methane detection algorithm parameters according to one embodiment of the invention in response to laser methane detector scanning of the leak of FIG. 6 where the scan occurred at a 0 degree angle along the curb.
Figure 9:
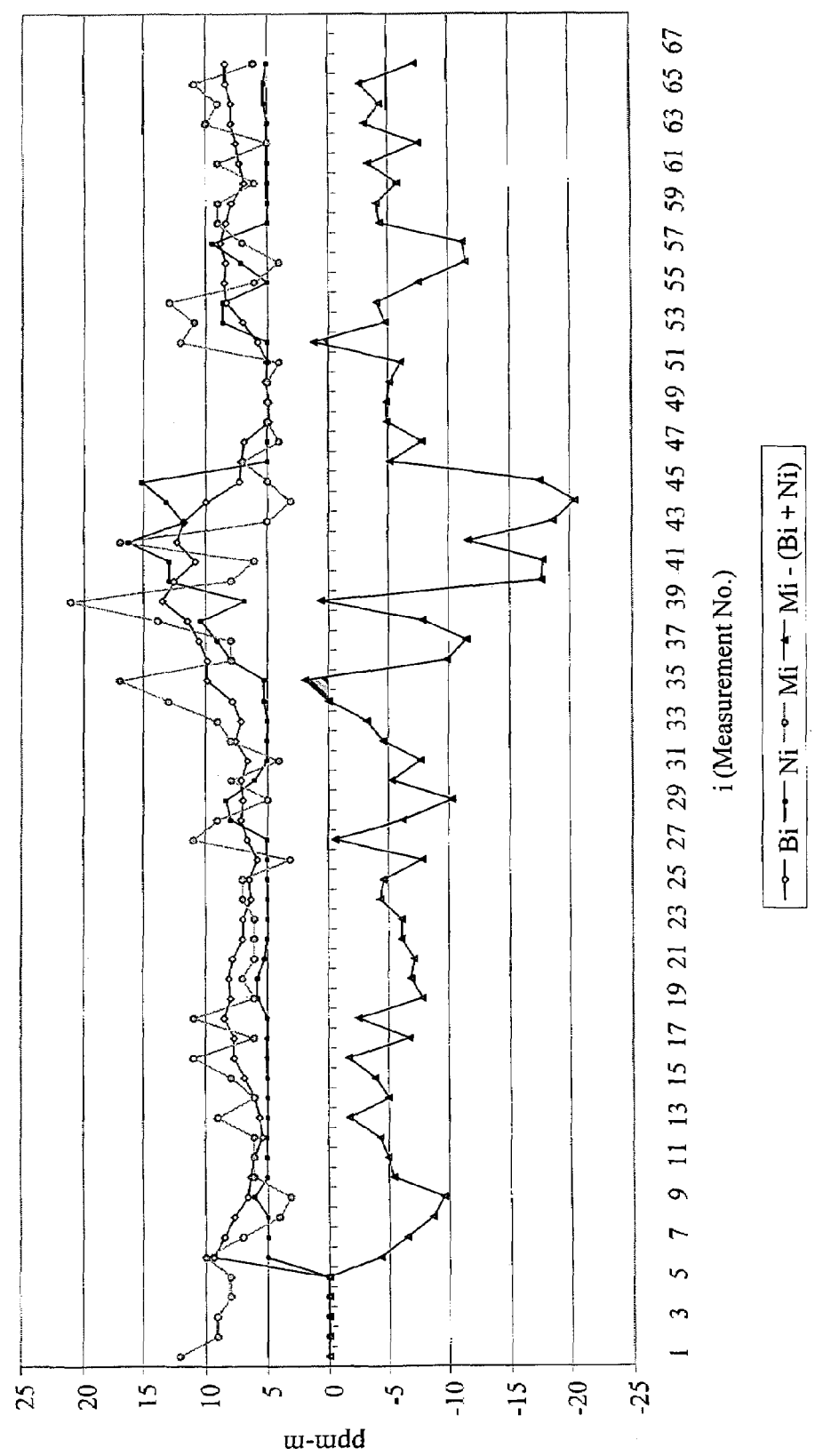
FIG. 9 is a line graph of some of the digital methane detection algorithm parameters according to one embodiment of the invention in response to laser methane detector scanning of the leak of FIG. 6 where the scan crossed over the granite curb.

FIGS. 6–8 are based on a 100 ppm leak in a roadside curb joint with detection by a laser methane detector according to one embodiment of the invention. For FIG. 6, scanning occurred across the face of the curb at a 90 degree angle from the opposite side of street. For FIG. 7, scanning occurred at a 45 degree angle about 25 feet from the leak. Scanning began in front of leak and proceeded up along the curb line past the leak. For FIG. 8, scanning occurred at a 0 degree angle (along the curb). Scanning started short of the leak and progressed up the curb line past the leak. FIGS. 6–8 all show consistent positive spiking of $M_i-(B_i+N_i)$ (shaded for easy identification) in the right portion of the graphs indicating detection of the leak. FIG. 9 shows data which was collected to observe the behavior when the beam crosses over the granite curb. In FIG. 9, there was no observable leak using a FID.

Referring back to FIG. 6, the data resulted from sweeping the laser beam from the road surface across a granite curb and onto a sidewalk. The initial $M_i$ spike at i=3 is suspected to result from optical differences (reflection, absorption, etc.) at the transition between the concrete driveway and the curb. The measured column density, and therefore the background and noise estimates, vary as the laser beam passes from one environmental condition to another. Although it did not in this case, the detection algorithm may present a false alarm if the signal response has a significant discontinuity because of environmental factors, e.g., transition from grass to asphalt, jumps in distance, distance etc. The various detection parameters are chosen to minimize false alarms due to environmental discontinuities yet to be responsive enough to detect an actual leak. However, the operator preferably understands this balance and can use this information to help distinguish a false alarm due to environmental factors from detection of a leak.

Figure 10:
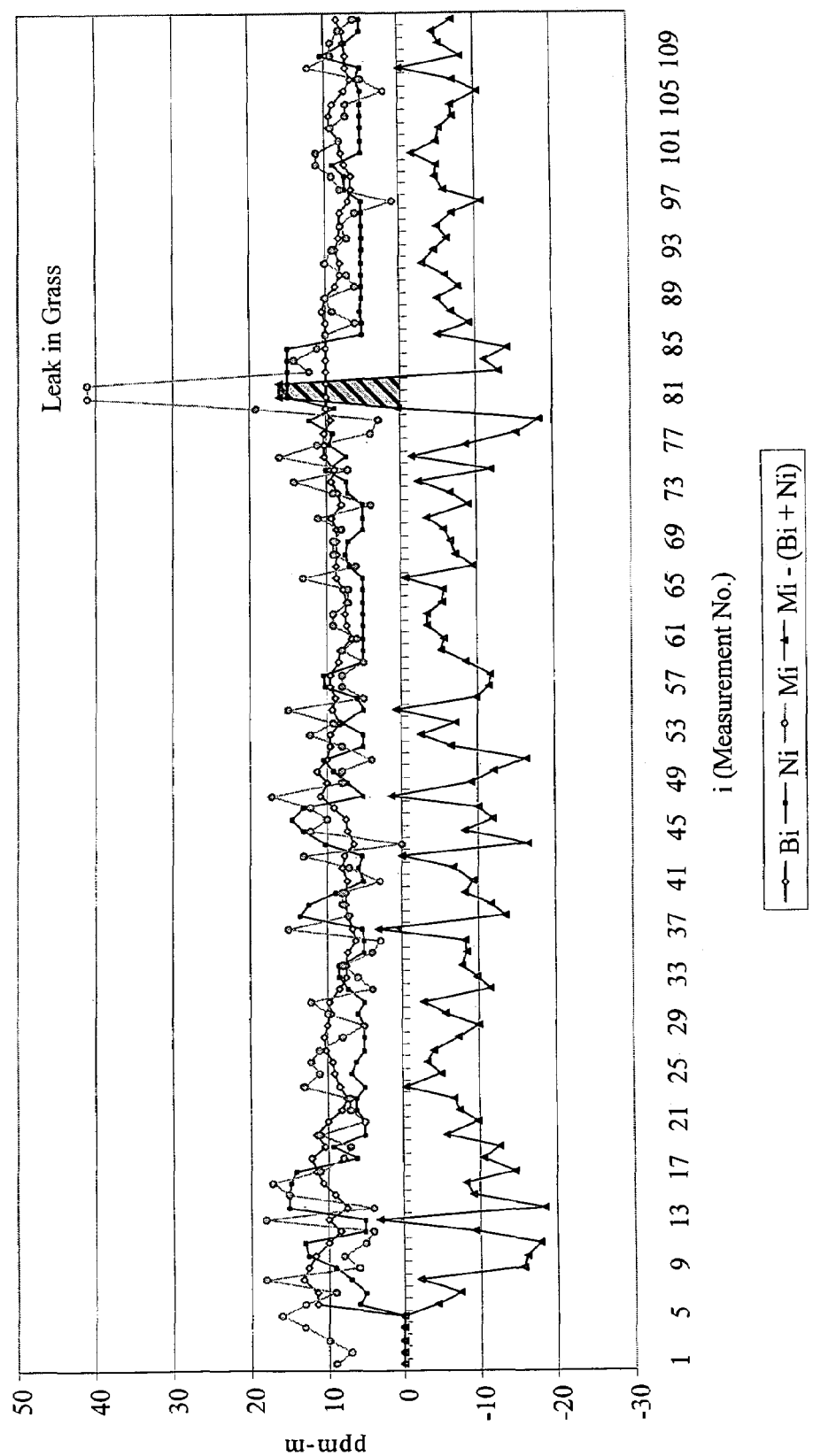
FIG. 10 is a line graph of some of the digital methane detection algorithm parameters according to one embodiment of the invention in response to laser methane detector scanning of a high concentration level leak resulting in a low volume gas cloud in the grass, where the scan occurred from the street, over the curb, onto the side walk, onto the grass, and past the leak.

FIG. 10 is based on a high concentration level leak with a low volume gas cloud located above a grass yard. There is also a small leak in the street nearby. Scanning occurred from the street (near the small leak), over the curb, onto the side walk, onto the grass, and past the high concentration leak. The small positive spike in $M_i-(B_i+N_i)$ at i=13 may have resulted from the small leak in the street at the start of the sweep. The larger spike in $M_i-(B_i+N_i)$ at i=81 shows the detection of the high concentration leak in the grass.

Referring to Equation 11, by setting the alarm level $A_L$, the user is determining the minimum $M_i-(B_i+N_i)$ level that warrants the user to investigate the area further. Two basic thresholds are preferred. First, $A_L$=20 ppm·m. If a high return of greater than 20 ppm·m above background/noise was observed, the user would accept this as indication of a possible gas leak in the area. This alarm level is generally suitable for both near and far scanning distances. Second, $A_L$=5–8 ppm·m. This alarm level is generally useful for scanning distances and surfaces that have minimal and constant background readings, i.e., scanning in the near field of approximately 20 feet or less. Typical background/noise levels are in the 5 ppm·m range while scanning at close range, and a typical "hit" is likely to be in the 10 to 15 ppm·m range. In the near field, any "hit" may be an indication of a possible gas leak in the area.

Figure 11:
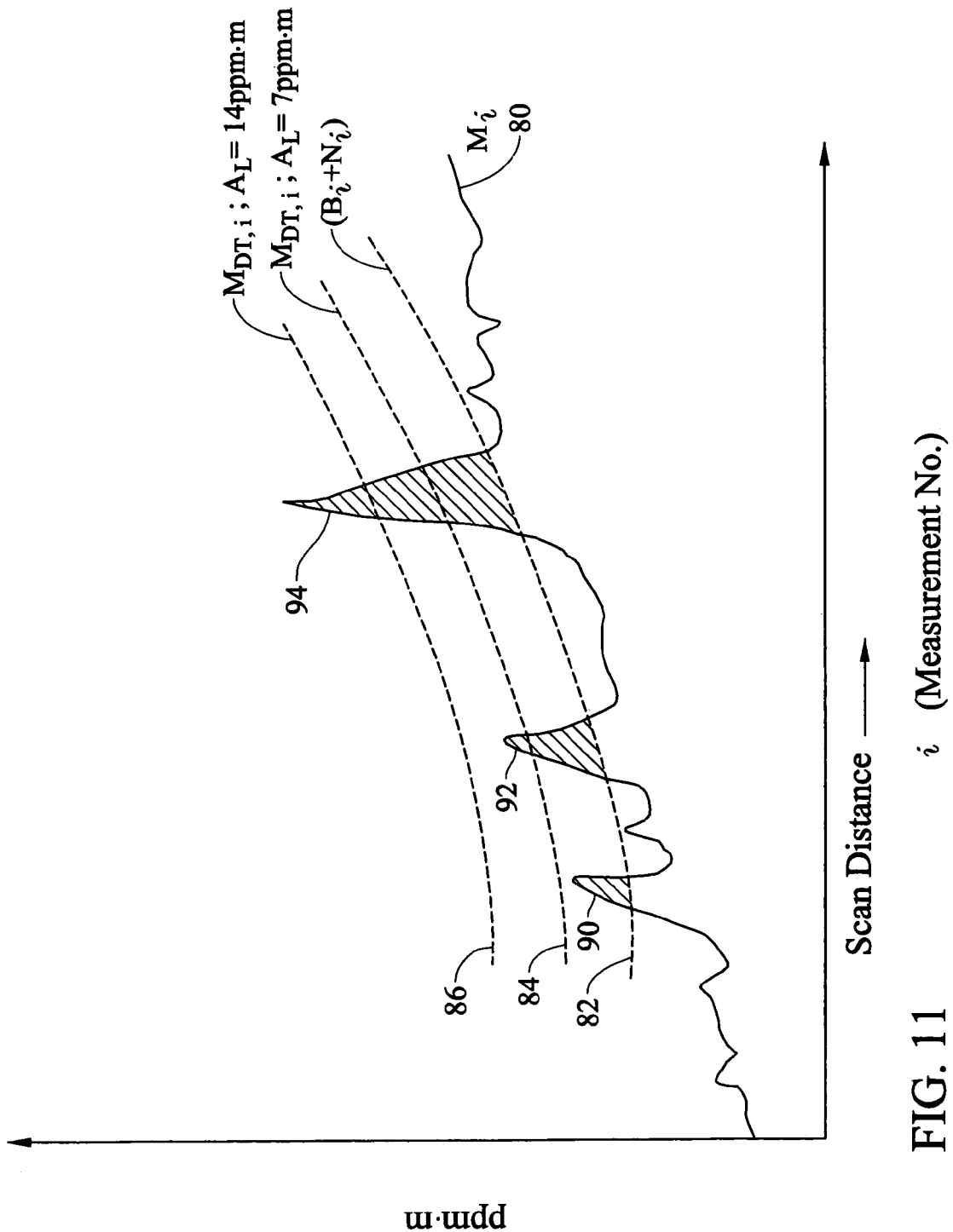
FIG. 11 is a line graph of some of the digital methane detection algorithm parameters according to one embodiment of the invention illustrating how various alarm set points affect the balance between detection of low level leaks and the false alarm rate.

Inherent in all automated detection methods is the probability of setting the alarm threshold $A_L$ too low and creating a high false alarm rate, or setting the threshold too high and missing detection of actual gas leaks. In some cases, there may be minimal signal difference between a low level leak $M_i$ reading and background readings. Consequently, the false alarm or false rest rates will be significantly altered by the selection of the threshold value. For example, FIG. 11 illustrates some of the preferred algorithm parameters for a hypothetical leak condition. The measured column density $M_i$ plot 80, a combined background and noise estimate $(B_i+N_i)$ curve 82, a first $M_{DT,i}$ curve 84 where the $A_L$=7 ppm·m, and a second $M_{DT,i}$ curve 84 where the $A_L$=14 ppm·m are shown. As the scan progresses in time, i.e., as i increases, the laser methane detector is focused to survey across a longer distance, increasing the laser beam length. The $M_i$ curve 80 has three peaks 90, 92, 94 (shaded for simplicity) where $M_i>(B_i+N_i)$, i.e., where $M_i-(B_i+N_i)>0$. Peak 90 is not due to a leak, but peaks 92, 94 are due to low concentration and higher concentration leak plumes, respectively. Curve 82 corresponds to $A_L$=0 ppm·m. At this level, the laser methane detector alarms (e.g., sounds a tone) at peaks 90, 92, and 94. Because the laser methane detector alarms at peak 90, a false alarm occurs. At lower alarm levels, e.g. 3 ppm·m, excessive false detections may occur. Curve 84 corresponds to $A_L$=7 ppm·m. At this level, a minimum level selected to prevent false alarms, the detector may be as sensitive to low level leaks as possible. False peak 90 is filtered by the detection algorithm, because $M_i<(B_i+N_i+A_L)$ at that point, but peaks 92 and 94 still cause an alarm. At $A_L$=14 ppm·m (curve 86), only peak 94 triggers an alarm. The alarm level may be increased to reduce excessive false alarms or to establish a more practical detection rate for very low level leaks.

In addition to comparing the methane column density reading $M_i$ to the detection threshold $M_{DT,i}$, if the $M_i$ methane column density reading exceeds an absolute level $M_{ABS}$, or if the $f_2$ return is above a predetermined set point while $f_1$ is low, then leak detection may be indicated. Detection based on absolute level accounts for sustained high-level readings or for conditions that generate a large background and variance estimates because user is standing in the middle of a methane cloud. The selection of the absolute detection level $M_{ABS}$ may vary. A level of $M_{ABS}$=100 ppm·m is preferred since it should be significantly higher than worse-case background and noise conditions. The complete detection algorithm of a preferred embodiment may be expressed as $$\text{if } ((M_i>M_{DT,i}) \text{ or } (\overline{M_i} \geq M_{ABS}) \text{ or } (f_1 \leq 25 \text{ and } f_2 \geq 1.0)) \quad (12)$$

then detection=TRUE else detection=FALSE where:
- $M_i$ is the calculated methane column density (ppm · m);
- $M_{DT,i}$ is the detection threshold for the ith reading;
- $\overline{M_i}$ is the mean methane reading over the n previous readings;
- $M_{ABS}$ is absolute methane set point;
- $f_1$ is the received first harmonic intensity; and
- $f_2$ is the received second harmonic intensity.

Alternatively, the $f_1$, $f_2$ condition, the absolute level condition, or both may be omitted from the algorithm if desired.

Having established a statistical method for detecting leaks from background gas levels, the algorithm should include a method to effectively communicate this information to the user. A first variant of an audio output can be implemented such that the output tone level is set to a constant pitch, e.g., 500 Hz, whenever there is detection and is silent when there is no detection. Because the tone is silent unless there is a leak detection, the user is not constantly subjected to a bombardment of tones between which he must decipher in order to identify a potential leak. The user will thus be more comfortable using the laser methane detector for longer periods, and leak conditions are more easily identified. However, the audio output algorithm may be further enhanced by extending the duration of the tone, once triggered. Because the detection algorithm tends to smooth out the data and reduce the actual width of the response, alarm conditions of only a few samples may be difficult for a user to hear. Extending the duration of the tone when there is a detection by only 1 or 2 samples may help the user hear a very short "hit." As another consideration, because during normal scanning with no leak detected the user hears no tone, an indication other than silence must be selected to alert the user to low light conditions or other errors. For example, if $f_1<10$ and $f_2<0.5$, then a pulsed tone with T=50 Hz, or other suitable indication, can be used to reflect the low light condition.

In a second audio output variant, the pitch of the output tone is relative to the strength of the detection. The tone is preferably silent when there is no detection. A simplified (not including extension of tone duration or error conditions) combined detection-tone algorithm may be expressed as if $((M_i > M_{DT,i})$ or $(\overline{M_i} \geq M_{ABS})$ or $(f_1 \leq 25$ and $f_2 \geq 1.0))$ (13)

then $T = c \cdot M_i = c \cdot k(f_2/f_1)$ else T=0 Hz where:
- T is the output tone level (Hz);
- $M_i$ is the calculated methane column density (ppm · m);
- $M_{DT,i}$ is the detection threshold for the ith reading;
- $\overline{M_i}$ is the mean methane reading over the n previous readings;
- $M_{ABS}$ is absolute methane set point;
- $f_1$ is the received first harmonic intensity;
- $f_2$ is the received second harmonic intensity;
- c is a tone coefficient, typically 10 Hz/ppm · m; and
- k is a conversion constant.

This embodiment combines the prior art advantage of the output tone pitch indicating the strength of beam return with the statistical methane detector algorithm and overall silent-use features. Tones may be generated by a tone generator or other suitable device.

Although the invention is described with regard to embodiments used for detection of methane or for natural gas leaks, the method and apparatus of the invention are not limited to methane leak detection. Methods and apparatus for detection of other gases besides methane or detection of gases for a purpose other than leak detection are within the scope of the invention. Further, the invention is not limited to use within field of utility companies.

The Abstract of the disclosure is written solely for providing the United States Patent and Trademark Office and the public at large with a means by which to determine quickly from a cursory inspection the nature and gist of the technical disclosure, and it represents solely a preferred embodiment and is not indicative of the nature of the invention as a whole.

While some embodiments of the invention have been illustrated in detail, the invention is not limited to the embodiments shown; it is apparent that modifications and adaptations of the above embodiments may occur to those skilled in the art. Such modifications and adaptations are in the spirit and scope of the invention as set forth herein:

What is claimed is:

1. A method of detecting the presence of a gas comprising the steps of, illuminating a target with a light beam from a laser having a wavelength generally corresponding to an absorption band of said gas, receiving at a detector a received portion of said light beam which is reflected from said target, sampling said received portion of said light beam to produce a series of measurements which are indicative of a concentration length product of said gas through which said received portion of said light beam has traveled, periodically determining a detection threshold from a statistical analysis of said series of measurements which estimates a threshold level above which a current measurement of said series of measurements is significant, comparing said current measurement of said series of measurements with a recent determination of said detection threshold, and producing a signal which indicates the presence of said gas at a level greater than said threshold level when said current measurement exceeds the recent determination of said detection threshold.

2. The method of claim 1 wherein said step of periodically determining a detection threshold includes the step of, periodically determining said threshold level from a statistical average of a first plurality of said series of measurements.

3. The method of claim 1 wherein said step of periodically determining said threshold level includes the step of, calculating an average of said first plurality of said series of measurements.

4. The method of claim 3 wherein, said first plurality of said series of measurements consists of a first number of consecutive measurements which are most recent in said series of measurements just prior to said current measurement.

5. The method of claim 3 wherein the step of, determining said background gas level estimate includes the step of calculating, $$B_i = \begin{cases} B_i & \text{for } \overline{M_i} - M_i \leq \Delta M \\ B_{i=1} & \text{for } \overline{M_i} - M_i > \Delta M \end{cases}$$

and $$\overline{M_i} = \frac{\sum_{x=i-n}^{i-1} M_x}{n},$$

respectively, where $M_i$ is an ith measurement of said series of measurements, $B_i$ is said background gas level estimate, $\overline{M_i}$ is an average of a number n of previous consecutive measurements of said series of measurements, and $\Delta M$ is a background change threshold value.

6. Then method of claim 1 wherein said step of periodically determining a detection threshold comprises the step of,
  periodically determining a measurement noise level estimate from a statistical variance of a second plurality of said series of measurements.

7. The method of claim 6 wherein said step of periodically determining a measurement noise level estimate comprises the step of,
  calculating a standard deviation of said second plurality of said series of measurements.

8. The method of claim 7 wherein,
  said second plurality of said series of measurements consists of a second number of consecutive measurements which are most recent in said series of measurements just prior to said current measurement.

9. The method of claim 6 further comprising the step of, determining said measurement noise level estimate by $N_i$ and $\hat{M}_i$ functions, $$N_i = \begin{cases} N_{LL} & \text{for } \hat{M}_i < N_{LL} \\ \hat{M}_i & \text{for } N_{LL} \leq \hat{M}_i \leq N_{UL} \\ N_{UL} & \text{for } \hat{M}_i > N_{UL} \end{cases}$$

and $$\hat{M}_1 = \sqrt{\frac{m \sum_{x=i-m}^{i-1} (M_x)^2 - \left(\sum_{x=i-m}^{i-1} M_x\right)^2}{m(m-1)}},$$

where $M_i$ is an ith measurement of said series of measurements, $N_i$ is said measurement noise level estimate, $\hat{M}_i$ is a standard deviation of a number m of previous consecutive measurements of said series of measurements, $N_{LL}$ is a lower noise limit, and $N_{UL}$ is an upper noise limit.

10. The method of claim 1 wherein said step of periodically determining a detection threshold includes the step of,
  including a user-set alarm level set point in said detection threshold.

11. The method of claim 1 wherein,
  said step of periodically determining a detection threshold from a statistical analysis of said series of measurements occurs for each measurement in said series of measurements.

12. The method of claim 1 wherein the step of producing a signal which indicates the presence of said gas comprises the steps of,
  producing no tone signal when said current measurement does not exceed the recent determination of said detection threshold, and
  producing a tone signal when said current measurement exceeds the recent determination of said detection threshold.

13. The method of claim 12 wherein the step of producing a signal which indicates the presence of said gas further comprises the step of,
  extending the duration of said tone signal beyond a time when said current measurement no longer exceeds the recent determination of said detection threshold.

14. The method of claim 12 further comprising the step of,
  producing said tone signal with a pitch which is indicative of the magnitude of said current measurement.

15. The method of claim 1 wherein the step of periodically determining a detection threshold from a statistical analysis of said series of measurements is completed in real-time or near-real-time.

16. A method of detecting the presence of a gas comprising the steps of,
  illuminating a target with a light beam from a laser having a wavelength generally corresponding to an absorption band of said gas,
  receiving at a detector a reflected portion of said light beam which is reflected from said target,
  sampling said reflected portion of said light beam into a series of measurements which are indicative of a concentration length product of said gas through which said received portion of said light beam has traveled,
  periodically determining a background gas level estimate by calculating a moving statistical average calculation of a first plurality of said series of measurements,
  periodically determining a measurement noise level estimate from a moving statistical variance calculation of a second plurality of said series of measurements,
  providing a user determined alarm limit,
  comparing a current measurement of said series of measurements with a function of a sum of a recent determination of said background gas level estimate, a recent determination of said measurement noise level estimate and said alarm limit, and
  indicating the presence of said gas when said current measurement of said series of measurements exceeds said function of said sum by a predetermined threshold.

17. An apparatus (11) for detecting the presence of a gas (20) comprising,
  a laser (30) capable of emitting light (18) characterized by a wavelength generally corresponding to an absorption band of said gas,
  an optical detector (32) capable of measuring said light disposed near said laser and positioned to receive a portion (24) of said light emitted by said laser and that is reflected back thereto by a distant target (22),
  a signal processing module (34) operatively coupled to an output of said optical detector and designed and arranged to produce a series of discreet measurements indicative of the concentration length product of the gas through which said portion of said light has traveled,
  a statistical detection processor module (50) operatively coupled to an output of said signal processing module and designed and arranged to statistically calculate a gas background estimate, and a measurement noise estimate, and to differentiate which of said measurements exceeds a sum of said gas background estimate and said measurement noise estimate, and a user provided alarm limit, and a user interface (38) operatively coupled to an output of said detection processor module.

18. The apparatus of claim 17 wherein said user interface comprises, a tone generator.

* * * * *